United States Patent [19]

Pardikes

[11] Patent Number: 5,372,421
[45] Date of Patent: Dec. 13, 1994

[54] METHOD OF INVERTING, MIXING, AND ACTIVATING POLYMERS

[76] Inventor: Dennis Pardikes, 12811 S. 82nd Ct., Palos Park, Ill. 60464

[21] Appl. No.: 12,958

[22] Filed: Feb. 3, 1993

Related U.S. Application Data

[63] Continuation of Ser. No. 540,910, Jun. 20, 1990, abandoned, which is a continuation-in-part of Ser. No. 352,689, May 10, 1989, abandoned, which is a continuation of Ser. No. 139,075, Dec. 28, 1987, abandoned, which is a continuation of Ser. No. 871,066, Jun. 5, 1986, abandoned.

[51] Int. Cl.$^5$ .............................. B01F 15/04
[52] U.S. Cl. .................... 366/137; 366/152; 366/162; 137/7
[58] Field of Search ............... 366/136, 137, 142, 151, 366/152, 155, 159, 160, 162, 165, 172, 176, 181, 263–264, 336–340, 342–343; 137/7, 12, 87–88, 98, 563, 565–566, 606, 896, 897; 422/135, 234, 256, 901

[56] References Cited

U.S. PATENT DOCUMENTS

| | | |
|---|---|---|
| 3,255,142 | 6/1966 | Terenzi . |
| 4,057,223 | 11/1977 | Rosenberger ............... 366/172 |
| 4,212,545 | 7/1980 | Lovasz et al. ............... 366/152 |
| 4,217,145 | 8/1980 | Gaddis ............... 106/170 |
| 4,218,147 | 8/1980 | Rosenberger ............... 366/162 |
| 4,274,749 | 6/1981 | Lake et al. ............... 366/161 X |
| 4,299,501 | 11/1981 | Patil et al. ............... 366/136 X |
| 4,472,215 | 9/1984 | Binet et al. ............... 422/163 X |
| 4,482,704 | 11/1984 | Luetzelschwab ............... 366/137 X |
| 4,522,502 | 6/1985 | Brazelton ............... 366/160 |
| 4,621,927 | 11/1986 | Hiroi ............... 366/160 X |
| 4,642,222 | 2/1987 | Brazelton ............... 366/160 X |
| 4,664,528 | 5/1987 | Rodgers et al. ............... 366/137 X |
| 4,747,691 | 5/1988 | Hoffland ............... 366/160 |
| 4,776,977 | 10/1988 | Taylor ............... 366/151 X |
| 5,018,871 | 5/1991 | Brazelton et al. ............... 366/168 |
| 5,061,456 | 10/1991 | Brazelton et al. ............... 366/165 X |

FOREIGN PATENT DOCUMENTS 580438 7/1959 Canada ............... 366/160

*Primary Examiner*—Timothy F. Simone
*Assistant Examiner*—Charles Cooley
*Attorney, Agent, or Firm*—Laff, Whitesel, Conte & Saret

[57] ABSTRACT

The inventive method inverts and activates polymer, and delivers it to an output at a relatively high concentration of polymer in an electrolyte fluid, such as water. The inversion and activation results from four steps: (1) premixing polymer and a diluent, (2) blending the premixed polymer/diluent in a derated centrifugal pump, (3) recycling a portion of the blended mix, and (4) suddenly relaxing the pressure to relax the polymer in the blended polymer/diluent mixture. A secondary source of the fluid is applied at the output to the high concentration in order to dilute it to a desired level of concentration. A pilot controlled valving system controls the secondary source of the fluid and maintains a uniform dilution despite any fluctuation in the delivery of the fluid to the activating system. A sensor at the output feeds back a control signal to maintain a uniform level of polymer activity in the outflow from the system. A check valve monitoring system gives an alarm if water seeps back toward a source of polymer which is to be activated.

9 Claims, 6 Drawing Sheets

METHOD OF INVERTING, MIXING, AND ACTIVATING POLYMERS

CROSS REFERENCE TO RELATED APPLICATION

This application is a continuation of Ser. No. 07/540,910, filed Jun. 20, 1990 (now abandoned), which was a continuation-in-part of Ser. No. 07/352,689, filed May. 10, 1989, (now abandoned) which was, in turn, a continuation of Ser. No. 07/139,075 filed Dec. 28, 1987, now abandoned, which was, in turn, a continuation of Ser. No. 06/871,066 filed Jun. 5, 1986, now abandoned.

BACKGROUND

This invention relates to means for and methods of mixing and activating or inverting polymers, at a high speed, and in either batch or continuous loads, while being able to control, select and maintain polymer concentration and activation.

The term "activation" is widely used to describe the chemical transition of polymer to a usable form. Recently, the terminology has tended to focus on how much activation has occurred with some arguing that there must be 100% activation before the word can be used. Since nothing is ever perfect, it is seen that if this argument is carried to the extreme, very little polymer would ever be 100% activated. As used herein, no such fine level of distinction is made. The word "activated", in its many forms, is intended to encompass the start of the process and everything occurring thereafter. Perhaps the word "inversion" might be more appropriate since it applies regardless of the degree of completion of the activating process.

Liquid or emulsion polymers are ionic-charged organic molecules which are soluble in water or another electrolytic fluid, which are herinafter simply called "water". Unactivated or neat polymers are encased by an oil carrier. In this phase, the molecule is coiled upon itself in a microgel form suspended in the oil carrier. Due to its charge, it tries to uncoil, but the oil carrier overcomes the charge and keeps it coiled.

Liquid polymers are used by various industries to simplify their industrial processes and make them more economical. For example, liquid polymers may be used for water purification and flocculation; may be used in automotive paint spray booths; may be used in the chemical industry to separate inorganics and solids from plant effluent; may be used in the coal industry to promote solids settling and to float coal fines; may be used in the petro-chemical industry to enhance oil recovery; may be used in the phosphate industry to improve recovery; may be used in the pulp and paper industry as dewatering aids and retention aids; or may be used in the steel industry to settle wastes. Those familiar with this art will readily perceive many other uses in many other industries.

Usually polymers are manufactured and shipped in a deactivated form to a location where they will be used. At that location, it is necessary to activate or invert the polymers before they can be used. Usually, that means that a polymer must be mixed with water or other electrolyte (solvent), or with a chemical, to provide an electrolyte which can change the polymer from an inactive state into an active state which can be so mixed. The process for so converting the polymer into an active state is one of imparting a sufficient amount of energy to the polymer. Reference may be made to U.S. Pat. Nos. 4,057,223, 4,218,147 and 4,217,145 for examples of prior art polymer activating systems.

The polymer encased in the oil phase is inactive. Therefore, its hydrocarbon surroundings must be emulsified or broken to allow the ionic molecule to uncoil or hydrate. This process of hydration is called activation or inversion. The way in which emulsion polymers are activated are to dilute them with water and to add enough mixing energy to emulsify the oil carrier and thus to enable the ionic charged molecule to uncoil. More particularly, the energy imparted to the inactive polymer includes a mechanical agitation which breaks down the hydrocarbon carrier phase, and thus enables water to reach and react with the long coiled molecule. Once that molecule is in water, like charges on the molecule repel each ocher and the molecule straightens and changes from the coil into a long and more or less straight "conformation". Until this conformational rearrangement occurs, the molecule is useless for most purposes.

The exact amount of energy required for an emulsion polymer activation is not known. However, there is an increase in the viscosity of the polymer, which is proportional to its stage of activation. This increase in viscosity is due to the uncoiled molecules intertwining with each other. The uncoiling of the molecules provide active sites for the attachment of foreign material in a medium. Then, the increased weight on these molecules settles them, carrying with them the settled material.

In the utilization of emulsion polymers, care must be taken to properly prepare the polymer. Different polymers require different amounts of energy for activation, tougher polymers require more force, while others need less force. Further, care must be taken not to overshear the molecules. Overshearing tends to break the uncoiled molecules, thus lowering their viscosity and making them less effective. Undershearing also is deleterious in that the polymer is then inefficient and uneconomical.

The known activating systems have required relatively long periods of time (such as an hour or so) in order to, for example, complete the inversion of the polymer. This long period of time increases the requirements for holding tanks during activation. Therefore, the relatively long period of activation time is relatively expensive. Also, the requirement for such a long term for activation greatly increases the capital requirements for the purchase of machinery when a system is operating continuously, as opposed to a batch system. Thus a faster polymer activating system is highly desired.

Primarily, the prior art used the batch method to invert liquid polymers. Polymer and water are delivered to a common mixing tank. Once in the tank, the solution is beat or mixed for a specific length of time in order to impart energy thereto. After mixing, the resulting solution must age to allow enough time for the molecules to unwind.

There are many different kinds of polymers which leads to a plethora of application requirements. It might be easy to build an entirely new custom designed system or machine for each and every different polymer activation job; however, the cost would then become prohibitive. This highlights the need for a great flexibility for a polymer activation system or machine, which in turn leads to the need for alternative mechanisms which may be added to or removed from the activating hydraulic circuits according to the then current needs.

One way to satisfy both the greater flexibility and a reduced system cost is to adjust the system to process a greater concentration of polymer. For example, instead of producing an output fluid which is 1% polymer, the system may be adjusted to produce a more concentrated fluid which is 2% polymer. Then, the concentrated 2% outflow may be diluted downstream to become 1% polymer, which would double the volume produced by a relatively small machine, to become the volume of a machine of twice the size, if it was originally designed to process a polymer as a 1% fluid. The activation process continues long after the discharge of the inverted polymer from the system outlet.

Merely adding more water in the primary dilution of a polymer might very likely wash away necessary inverting agents, called "activators" or surfactants which are useful in emulsifying the hydrocarbon carrier. For example, a particular use of a particular polymer might require a tenth percent (0.1) polymer solution, but the polymer would lose necessary chemical components if an effort is made to dilute the polymer this much in a single pass through the system. Once a polymer is inverted, there is little, if any, need for retaining these chemical activators. Therefore, the invention presents the opportunity to invert a polymer solution to, say, one percent. (1.0) Once the polymer is inverted, the solution may be diluted downstream to reduce the one percent solution to become a tenth percent solution. Hence, in this example, with the invention, it is possible to produce a tenth percent solution that could not have been produced heretofore.

Two examples of dilution systems which have been designed with these thoughts in mind are found in Rosenberger's and Brazelton's U.S. Pat. Nos. 4,128,147 and 4,642,222. Each of these patents shows a method of adding dilution water to an inverted polymer as it exits a system, thereby theoretically enabling the system to deliver higher concentrations of polymer which are then diluted to give a greater volume of total output. However, it is thought that each of these patents contain basic design flaws since each subjects activated polymers to abrupt pressure changes or additional mixing once the polymer has reached its extended state. That is the output lines of these patents include pressure regulators and/or mixing devices which will create a higher upstream pressure as compared to a lower downstream pressure. Once a polymer is activated, such a pressure change or additional mixing may cause shear and break the now linear polymer molecule, thereby damaging or destroying the polymer.

According to FIG. 1 of the Rosenberger patent the polymer solution is subject to a pressure drop as it passes through the second fixed flow rate regulator. Brazelton teaches the reduction or increase in the input of polymer flow to his mixing system instead of varying the water flow.

SUMMARY

Accordingly, an object of the invention is to provide new and improved means for and methods of activating polymers.

Another object of the invention is to provide flexible polymer activating systems or machines, which may be adapted to fit the needs of particular polymers which are being processed. In particular, an object is to provide means for activating concentrated polymer solutions and for thereafter introducing downstream a secondary dilution to bring the concentrate into a useful range before the molecules become fully hydrated.

Yet another object of the invention is to provide an efficient system and method for activating liquid polymers. Here an object is to provide an automatic, continuous system which is able to vary the output rate of inverted polymer, while automatically maintaining the amount of energy imparted thereto and while maintaining a desired concentration of the polymer.

In particular, an object is to monitor the level of active solids in an outflow from the system and to provide system control functions in response to the level detected during the monitoring in order to maintain greater stability.

In keeping with an aspect of the invention, the activation of a polymer occurs in four stages, which are: pre-mixing, blending, recycling, and a final sudden pressure reduction. The pre-mixing occurs in a manifold containing a static mixer. The blending occurs within a centrifugal pump where water is blended with the polymer. The outflowing stream from the centrifugal pump divides with part of the outflow feeding back through the static mixer and centrifugal pump. The other divided part of the outflow is delivered to a mixing pressure regulator where the pressure imparted by the centrifugal pump is suddenly reduced to, or near, atmospheric pressure. This suddenly relaxes the coiled, long polymer molecule to hasten its straightening. This system provides three different kinds of shear which are imparted during the inversion of the polymer fluid. First, there is a boundary layer shear occurring in the centrifugal pump. Second, there is a visco-elastic shear at an orifice where the polymer fluid flows faster at the center of the orifice than at the periphery of the orifice. Third, there is a structuring shear when the pressure suddenly reduces as the polymer solution passes through the mixing pressure regulator. In one exemplary inventive system, the entire inversion requires only about one second.

The invention enables an adjustment which controls the amount of energy introduced into the polymer for inversion. Once the relationship between the amount of introduced energy and the output rate is established, the inventive system automatically compensates for variations therein.

The system also provides controls for varying the concentration of the polymer. A secondary fluid delivery system may dilute the concentrated polymer after it is inverted.

BRIEF DESCRIPTION OF DRAWINGS

Preferred embodiments of the invention are shown in the attached drawings, wherein.

DESCRIPTION OF PREFERRED EMBODIMENTS

Figure 1:
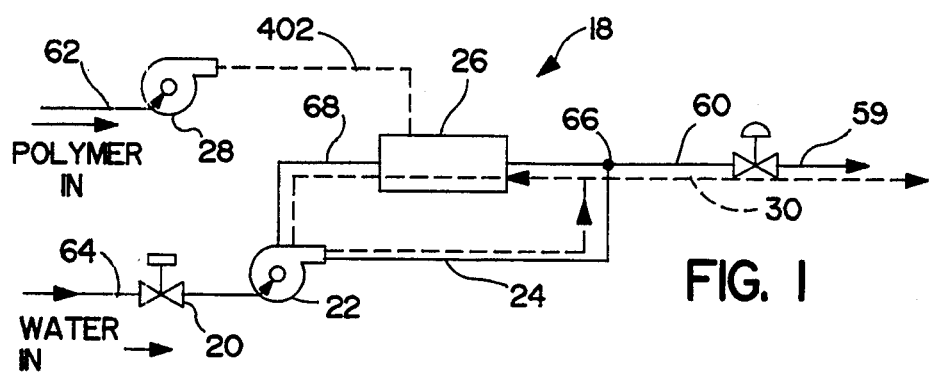
FIG. 1 schematically shows the principles of an inventive system having two inputs, which are for water and for the polymer that is to activated.

In FIG. 1, the polymer inverting and activating system 18 components are an input throttling valve 20 for controlling the ratio of water to polymer, a centrifugal pump 22 for introducing the water, a closed mixing loop 24, a pre-mixing manifold 26, and a centrifugal pump 28 for introducing the polymer. The water and polymer first meet in the pre-mixing manifold 26, the water flow being indicated in FIG. 1 by solid lines and the polymer flow being indicated by dashed lines. Valve 20 may be set to provide a ratio of water to about 1% polymer, in one example, with a useful ranger of ratios being in the order of 0.25 to 15% polymer. Associated with valve 20 may be a meter (not shown) which is calibrated in gallons per minute. By an adjustment of the valve 20, one can also select the desired output of the system, or a more highly concentration of inverted polymer solution.

The mixing pressure regulator 30 is critical in three areas. It is used to maintain a constant net positive discharge head on the booster module or centrifugal pump 22, which is an important consideration in the hydraulics of the system. It controls the amount of recycling which occurs in the recycle stage. It provides a variable pressure drop zone in the final stage and enables the operator to select a proper amount of mixing energy, based on the type and concentration of polymer being processed. The higher solids polymers and higher solution concentrations require more mixing energy than usual.

Figure 2:
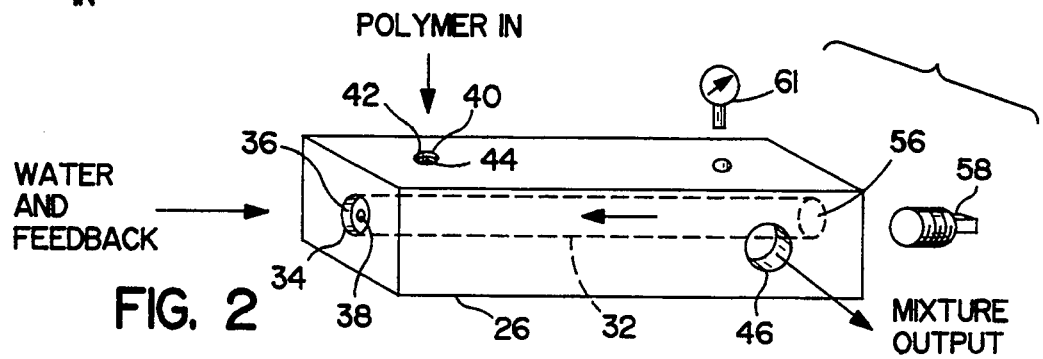
FIG. 2 is a perspective view of a pre-mixing manifold.

In greater detail, the mixing manifold 26 (FIG. 2) is, for example, a solid block of metal having a central bore 32 extending through substantially its entire length. The bore 32 stops short of a counterbored and threaded input opening 34, to form a bulkhead 36. An orifice 38 of fixed diameter is formed in the center of the bulkhead 36 to establish communication between the water inlet hole 34 and the central bore 32, with a flow rate that is controlled by the orifice diameter. The polymer solution experiences an extrusion type of shear as it passes through the orifice 38.

TABLE I

AN EXEMPLARY FLOW RATE AND RECYCLE VOLUME IN ONE EXEMPLARY SYSTEM

| TYPE OF PUMP | DIAMETER OF ORIFICE 38 | SOLUTION OUTPUT (GPM) | RECYCLE VOLUME GPM |
|---|---|---|---|
| 054 AnCAT | 3/32" to 3/16" | .25 to 10 gpm | 1.85 @ 40 psi to 8.12 @ 60 psi |
| L-10 AnCAT | ⅛" to ¼" | 3 to 10 gpm | 2.56 @ 30 psi to 14.5 @ 60 psi |
| L-20 AnCAT | ⅛" to ¼" | 3 to 20 gpm | 2.56 @ 30 psi to 14.5 @ 60 psi |
| L-30 AnCAT | ¼"to ⅜" | 3 to 30 gpm | 2.56 @ 30 psi to 32.5 @ 60 psi |
| L-60 AnCAT | 3/16" to ¼" | 5 to 60 gpm | 5.75 @ 30 psi to 57.8 @ 60 psi |
| L-80 AnCAT | 3/16" to ⅜" | 5 to 80 gpm | 5.75 @ 30 psi to 90.4 @ 60 psi |
| L-100 AnCAT | 3/16" to ⅜" | 5 to 100 gpm | 5.75 @ 30 psi to 130.0 @ 60 psi |

The last or recycle column indicates that the recycled or returned output from the derated pump 15 is in the order of about 5% to 70by volume. These figures are derived from a Cameron Table, which a conventional tool for hydraulic engineering. The converse statement would be that the outflow is 95% −30% by volume.

A first threaded hole 40 leads to another bulk head 42 between the entrance to the counter bored and threaded hole 40 and the central bore 32. An orifice 44 is formed in the bulkhead 42 to establish communication and to control the flow rate between the hole 40 and the central bore 32.

The output port 46 is in direct communication with the central bore 32 to give an unimpeded outflow of a mixture of polymer and water.

Figures 3A, 4:
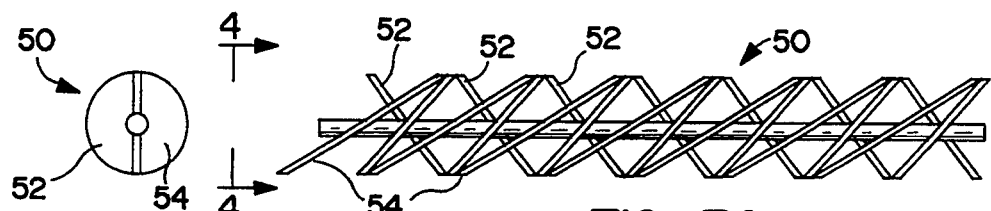
FIGS. 3A and B are two plan views (rotated by 90° from each other) a static mixer which is used inside the manifold of FIG. 2.
FIG. 4 is an end view of the static mixer, taken along line 4—4 in FIG. 3A.
Figure 3B:
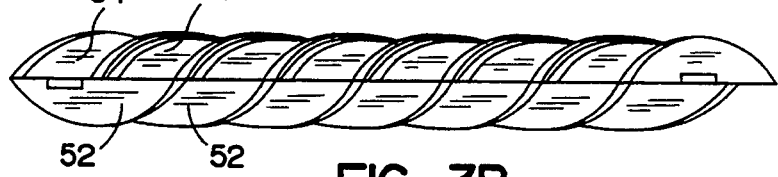

A static mixer 50 (FIGS. 3,4) comprises two sets of semi-elliptical baffles which are set at an angle with respect to each other so that the over all end view configuration is a circle (FIG. 4). The baffles 52 (FIG. 3A) on one side of the static mixer are a series of spaced parallel plates. The baffles 54 on the other side of the static mixer are Joined on alternate ends to give an over all zig-zag appearance. The outside diameter of the static mixer corresponds to the inside diameter of the central bore 32. Therefore, the static mixer 50 slides through an end opening 56 and into the bore 32. Thereafter a plug 58 seals off the end of the bore. In one embodiment, the static mixer 50 is a standard commercial product from TAH Industries of Inlaystown, N.J.

Water is introduced through the centrifugal pump 22 and into the mixing loop 24 (FIG. 1). The flow of water is controlled and metered by the throttling flow valve and meter at 20. The beginning stages of activation or the pre-blend stage occurs inside the centrifugal pump assembly 22.

The centrifugal pump 22 is a modified commercial item which is derated on the high end of its output flow by a factor in the order of 2 to 7, for example, for most applications. On the low end of its output flow, the derating factor may be much higher. That is the diameter (for example) of the impeller is trimmed to give a derated performance wherein there is a larger amount of stirring and mixing per volume flow, as compared to what might normally be expected from standard commercial centrifugal pump. Other techniques for derating an impeller including changing a pitch of the blades, thinning the width of blades, and the like.

Derating is also controlled by an adjustment of the water inlet flow. In greater detail, by way of example, a centrifugal pump usually has a series of flow charts which are supplied by the manufacturer. One flow chart, which may be the one normally used, may describe how the pump could provide a flow of 20 gallons per minute to the top of a 40 foot head, for example. Another flow chart may describe how the same pump could be operated at a different speed to provide five times that capacity, or at 100 gallons per minute to the same 40 foot head, in this particular example.

According to the invention, the pump is operated, for example, in the manner described by the manufacturer to deliver 100 gallons per minute, but the diameter of the impeller is reduced until the delivery returns to 20 gallons per minute, while the pump continues to be operated in the manner which the manufacturer suggests for 100 gallons per minute. Thus, in this particular example, the centrifugal pump has been derated by a factor of 5 (i.e. derated from 100 to 20 gallons per minute). After derating, the increased impeller speed, which is normally required to deliver 100 gallons per minute imparts a higher level of energy to the mixed fluid, without increasing the volume of fluid output.

The following chart illustrates a number of different centrifugal pumps which may be used for polymer injection at pump 28.

| TYPE PUMP | FLOW RATE |
| --- | --- |
| 054 AnCAT | 0–864 gpd |
| L-10 AnCAT | 0–2160 gpd |
| L-20 AnCAT | 0–4320 gpd |
| L-30 AnCAT | 0–6480 gpd |
| L-60 AnCAT | 0–12,960 gpd |
| L-80 AnCAT | 0–17,280 gpd |
| L-100 AnCAT | 0–21,600 gpd |

In pump type L-60, the impeller diameter was 5 inches; in pump type L-S0, it was 6 inches, and in pump type L-100, it was 6.25 inches.

The unactivated or neat polymer is introduced through the premix manifold 26 and into the mixing loop 24 by a variable speed, positive displacement pump 28 which delivers the polymer at a rate which achieves, a range of desired concentrations. Because the centrifugal pump 22 is derated, it causes a desirable mixing shear of the polymer. A calibration column (not shown) is provided to correlate the variable speed pump 28 to its capability to deliver the unactivated polymer at a rate which accurately obtains the desired concentration. The pump 28 is not modified and merely delivers the polymer to the mixing manifold 26.

The mixed water and polymer solution is recycled, via loop 24, back through the premix manifold 26 and the booster module (derated centrifugal pump 22) which continues to boost the level of the activation or inversion of the polymer.

The final stage of polymer inversion is controlled by the mixing pressure regulator 30. The polymer solution passing through the regulator 30 experiences a sudden and abrupt pressure drop which further inverts the solution. The pressure drop causes a third kind of shear of the polymer. This pressure drop is adjustable and represents an important factor in the development of the inversion of polymer molecules. The pressure regulator 30 is a standard commercial item.

More specifically, the mixing pressure regulator 30 is provided in the mixing loop to enable a discharge of the inverted polymer at a desired level of activation while, maintaining a net positive suction head in the centrifugal pump to prevent cavitation. Once the desired output rate and level of inversion is selected, the mixing pressure regulator 30 automatically compensates for any surging or ebbing flow which is attendant upon changes in the output flow rate. Thus pressure regulator 30 maintains the desired level of inversion in the centrifugal pump 22.

It should now be apparent that the mixing pressure regulator is critical in three areas. It is used to maintain a constant net positive discharge head on the booster module, which is an important consideration in the hydraulics of the system. It controls the amount of recycling which occurs in the recycle stage. It provides a variable pressure drop zone in the final stage and enables the operator to select a proper amount of mixing energy, based on the type and concentration of polymer being processed. The higher solids polymers and higher solution concentrations require more mixing energy than usual.

Regulator 30 is set to cause a sudden and abrupt relaxation of pressure, from the pressure in line 60 to or near atmospheric pressure. This sudden and abrupt relaxation causes an effect which is somewhat similar to the aging which occurs in a holding tank in prior art systems. A limiting factor is that the pressure regulator 30 can not be adjusted to operate at any level which causes cavitation in the derated centrifugal pump 22. The inverted polymer is delivered at output 59 for any suitable further use.

The solution output of the system with the various pump described above may be as follows:

| 054 AnCAT | .13 to 10 gpm |
| --- | --- |
| L-10 AnCAT | 3 to 10 gpm |
| L-20 AnCAT | 4 to 20 gpm |
| L-30 AnCAT | 4 to 30 gpm |
| L-60 AnCAT | 5 to 60 gpm |
| L-80 AnCAT | 5 to 80 gpm |
| L-100 AnCAT | 5 to 100 gpm |

The system also has a flow sensor (not shown) which senses the flow rate of the solution in the system. If a low water flow rate condition is sensed, (i.e. a flow below three gallons per minute for the L-10 pump), the system is automatically shut down and alarms are sounded. Further, a compound gauge 61 in the mixing loop provides means for a visual inspection of the operating conditions of the pump.

In operation, the invention provides an automatic system for inverting emulsion polymers at desired output rates and desired levels of activation. The system provides homogeneous, inverted, solutions at desired concentrations. The system, in fact, is inexpensive, reliable, and provides variable capabilities which are not offered by other known systems.

More particularly, the system takes in polymer at inlet 62 and water at inlet 64. The throttling valve 20 is set to regulate the amount of inflowing water and, therefore, the ratio of water to polymer. By adjusting valve 20 a more highly concentrated polymer solution may be produced. For example, a solution which is 1% polymer may be increased to a solution which is 2% polymer by a suitable adjustment of valve 20.

The diameters of the pipes, apertures, impedance of the static mixing device 50, etc. cause an outflow of derated centrifugal pump 22 to divide at point 66. The ratio selected for the division depends upon the nature of the product. In an exemplary system, about 60% of the outflow of derated centrifugal pump 22 passes through pipe 60 and the pressure regulator 30 to the output of the system. The remaining approximately 40% of the outflow from derated centrifugal pump 22 recirculates to the pre-mixing manifold 26, from which, it is fed back at 68 to the derated centrifugal pump 22. Thus, the feedback loop 24, 66, 26, 68, 22 always contains both the combination of a previously mixed solution of water and polymer and a new mixture of fresh stock and a feedback mixture.

It should now be clear that the inventive system has four stages: pre-mix, blend, recycling, and final stage. The pre-mix occurs in the mixing manifold 26 when the raw polymer first meets back fed polymer solution. The turbulence caused by baffles 52, 54 (FIG. 3) of the static mixer 50 tends to thoroughly mix the polymer and polymer solution, but the oil carrier suspending the coiled polymer molecule may remain unbroken.

The blend stage starts in the centrifugal pump 22 where the oil carrier begins to be or is broken, at a first level of inversion.

The recycling stage occurs in the feedback loop 24 where about 40% of the outflow of pump 22 continues to receive an imparted amount of energy to enhance the inversion process. A level of equilibrium and stability is soon reached wherein the majority of the hydrocarbon carrier is emulsified by the time that the outflow reaches the outlet pipe 60, where the polymer is inverted.

The final stage occurs when there is a sudden pressure drop in regulator 30 which relaxes the polymer molecule. Then, the similar charges along the long polymer molecule repel each other and cause it to straighten in response to the sudden reduction of pressure in regulator 30. The resulting inverted polymer is delivered from output 59 to any suitable device.

Figure 5:
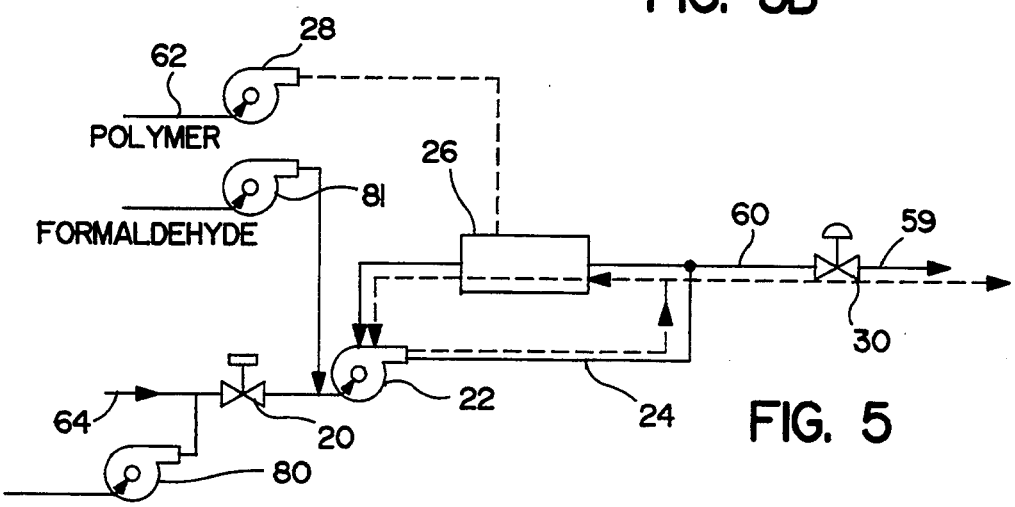
FIG. 5 is a schematic showing of a more sophisticated version of the system of FIG. 1 with provisions for introducing one or more chemicals which may be used in the electrolyte for activating the polymer.

The principles and the apparatus described thus far may be expanded and modified to provide systems which are custom designed for inverting various polymers in various electrolytes. These changes are illustrated in FIG. 5 where the format of the piping system has been modified to mix a polymer with, not only water, but also additional chemicals. In this particular example, the polymer is mixed with dimethylamine ("DMA") and formaldehyde. In its pure form, DMA is a highly flammable material which should not be brought into a factory. Therefore, DMA is introduced via a pump 80, the output of which is connected to the water input pipe 64 while it is outside the factory and before it reaches the throttle valve 20. After the DMA is mixed with water, it may be safely pumped into the factory.

The formaldehyde may safely be handled within a factory area; therefore, it is introduced via pump 81 which may be at any convenient location. The formaldehyde is injected into the mixture of water and DMA before it reaches the derated centrifugal pump 22 and the polymer.

The remainder of the system in FIG. 5 is the same as the system of FIG. 1. Therefore, it will not be described again. The out flow from pressure regulator 30 is a composition comprising a polymer mixed into a carrier of water, DMA, and formaldehyde.

Figure 6:
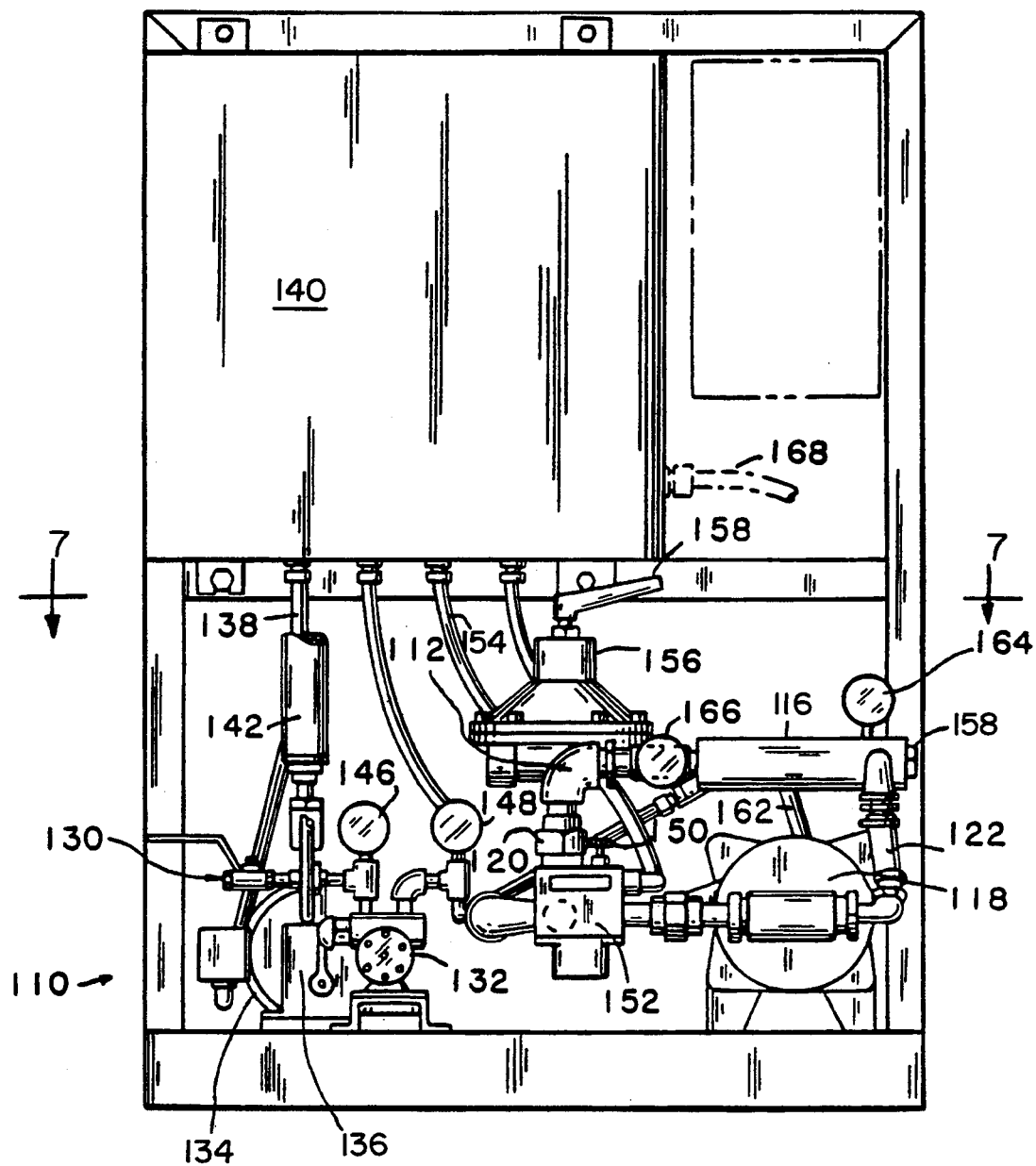
FIG. 6 is a front plan view of a system incorporating the invention.
Figure 7:
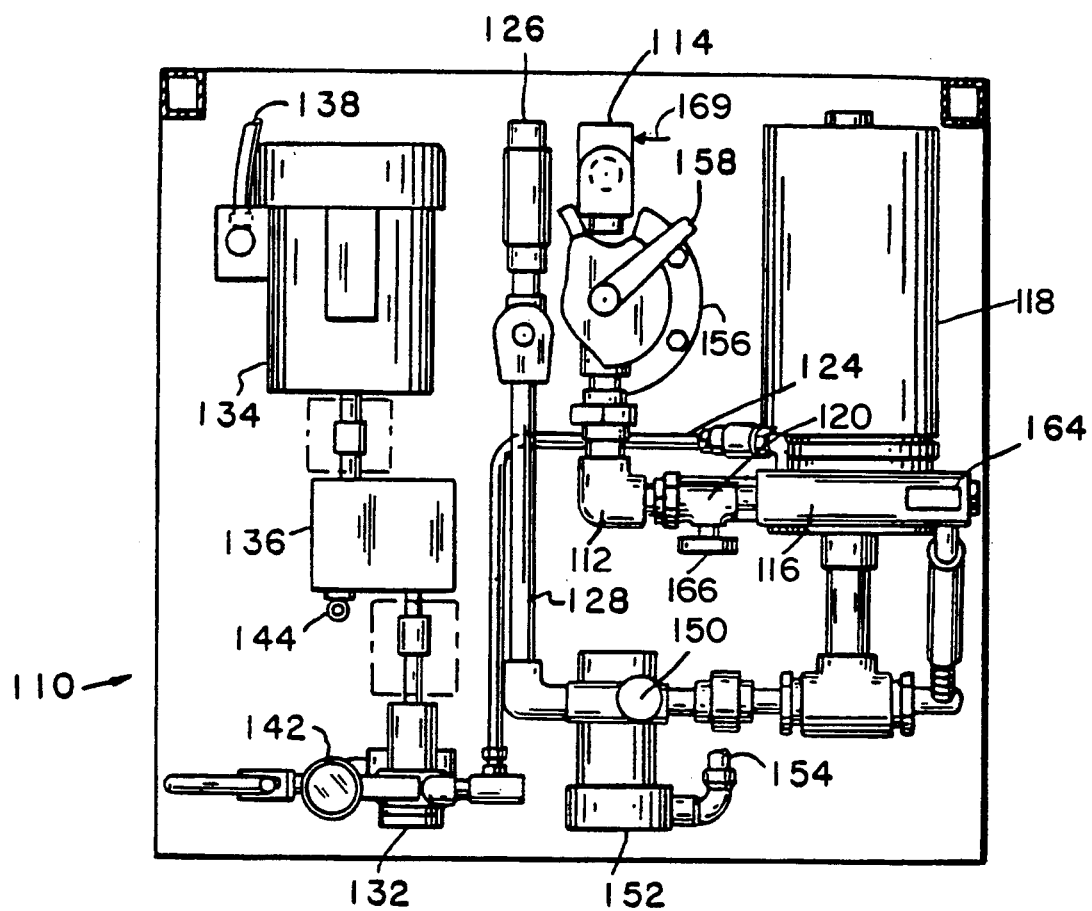
FIG. 7 is a plan view of the inventive system taken along lines 7—7 of FIG. 6.

FIGS. 6 and 7 shows a practical embodiment of an inventive system which incorporates the principles set forth in FIGS. 1-5. The system 110 is adapted to receive water and neat emulsion polymer in a mixing loop 112 in order to mix and invert the emulsion polymer at desired levels of energy. The system 110 further provides a continuous output of inverted emulsion polymer at desired rates through discharge outlet 114 where a sensor means may sense an active level of the polymer.

The mixing loop 112 includes a static mixing manifold or chamber 116 and a booster module or centrifugal pump 118 in fluid communication with each other through conduits 120 and 122. The unactivated or neat polymer is introduced through conduit 124 and into the mixing loop 112, for inversion, in the premix manifold or chamber 116. The water is supplied to a water inlet 126 which is in fluid communication with the mixing loop 112 through conduit 128.

Neat polymer is supplied from a source to the conduit 124 through shut-off valve 130 and pump 132. The system 110 is capable of automatically selecting the desired concentration of the inverted polymer once the desired flow rate of water is selected. This is accomplished by motor 134 coupled through gearbox 136 to the pump 132. The motor 134 receives its power from control panel 140 through electrical cable 138. The gearbox 136 enables an adjustment of the polymer feed rate through the pump 132 to the mixing loop 112.

The gearbox 136 is calibrated for each polymer which is utilized, because different solution concentrations produce different flow rates, for the same pump speed. The calibration is accomplished by closing shut-off valve 130 and by filling calibration column 142 with the polymer which is to be used. The calibration column 142 supplies its polymer to the pump 132. By correlating the rate of decrease of polymer in the column 142 to an adjustment member 144 on the gearbox 136, the polymer is delivered at a selected rate to the mixing loop 112. The shut-off valve 130 can then be opened to supply polymer at the desired rate.

Gauges 146 and 148 are coupled to the inlet and discharge sides, respectively, of the pump 132. These gauges provide a visual inspection of proper pump operation. Gauge 146 is a vacuum pressure gauge and indicates suction pressure of the pump. Gauge 148 monitors the discharge pressure of the pump. High level values on gauge 148 warn of blockage in the pump 132 or in the premix manifold or chamber 116 and lead to a deactivation of the system in order to ascertain and correct the cause of a malfunction.

The water is supplied to the mixing loop 112 via the conduit 128, a metering valve 150, and a flow rate indicator 152. The flow rate indicator 152 is calibrated in gallons per minute. By adjusting valve 150, one can select the desired rate of output of inverted polymer solution. The flow rate indicator 152 includes a low flow sensor. When a low flow condition is sensed in the system, an impulse is sent through electrical cable 154 to the control panel 140, which deactivates the system and sounds an alarm to alert an operator.

A mixing pressure regulator 156 communicates between the discharge outlet 114 and the mixing loop 112. The pressure regulator 156 contains an adjustment 158 for varying pressure within the mixing loop 112 to achieve a desired level of inversion of the emulsion polymer.

The booster module or centrifugal pump 118 supplies a motive force for mixing the polymer and water and for moving it through the mixing loop 112. The centrifugal pump 118 receives its power from the control panel 140 via cable 162. A gauge 164 is provided to visually inspect the operating condition of the pump 118. The gauge 164 is a compound gauge which is coupled to the premix manifold or chamber 116, to indicate the suction pressure of the pump 118. The conduit 120 includes a visual flow indication viewing window, for the mixing loop. Gauge 166 is coupled to the conduit 122 and gives values for the mixing pressure within the mixing loop.

The discharge outlet 114 discharges the inverted polymer either to a tank (not shown) or directly to a processing system (also not shown). Cable 168 communicates between the control panel 140 and the tank. When a predetermined level of active solids in the inverted polymer is sensed by a sensor 169 at discharge outlet 114, the control panel 140 deactivates or otherwise controls the system.

Once the desired levels of output and energy levels are selected, the system automatically operates the pressure regulator 156 to change the flow rate of the water to maintain the level of pressure in the mixing loop 112 which provides the desired level of the polymer inversion energy. Pressure within the mixing loop 112 dictates how much polymer recirculates, which in turn is directly proportional to the level of inversion energy. Therefore, with an increase in mixing pressure, via the mixing pressure regulator, the pressure in the loop increases which means more polymer recirculation. All of this is carried out by controls in panel 140 acting, in part, responsive to sensor 169.

The mixing loop 112 not only provides a balance to achieve a desired output rate and a desired level of inversion energy, but also provides a regulation to prevent a cavitation of pump 118. In order to get a flow rate out of the pump 118, it is necessary to supply it with its net positive suction head ("NPSH") requirement. Cavitation or a boiling of the liquid occurs if there is a failure to supply the pump 118 with its required NPSH. Therefore the regulator 156 and valve 150 balance the loop 112 and provide variations in the output rate and in the level of inversion energy, within ranges to regulate the NPSH requirement of pump 118.

The system is an automatic, efficient, low cost apparatus for mixing and inverting emulsion polymers. More particularly, the system 110 provides an ultimate control over an inverted polymer concentration which is in the range of about 0.10 to 15 percent. Also, the system 110 automatically provides a variable rate output, while maintaining critical mixing pressures for the introduction of controlled mixing energy to the emulsion polymer. Thus, the system may be either shut down or adjusted in response to an output sensor 169 in order to insure a proper inversion level and to maintain quality control.

An addition of secondary dilution enables the system to operate in a manner where a relatively small, low volume, low cost system may increase its productive output to match that of a much larger and high cost machine. Also, the secondary dilution enables a system to invert polymers in a manner which is much simpler, straight forward, and easier than was possible heretofore. In fact, it at least theoretically opens the door to an activation of polymers which might not have been subject to proper inversion heretofore.

The system described above (FIG. 1) has only a "primary dilution" between the inputs 62, 64 and output 59. The primary dilution results from the mixture of polymer and water in a ratio selected by valve 20. The outflow from pressure regulator 30 may have characteristics which are predetermined by the polymer being activated and the user's needs. If an effort is made to use a simplistic approach of directly producing a 0.1% solution, the raw water or other electrolyte forming the primary dilution would result in "surfactant washout". If an effort is made to simply double the output of the system by running more polymer and water through the system, the controls placed within the system would be overcome thus producing a low quality polymer solution.

Figure 8:
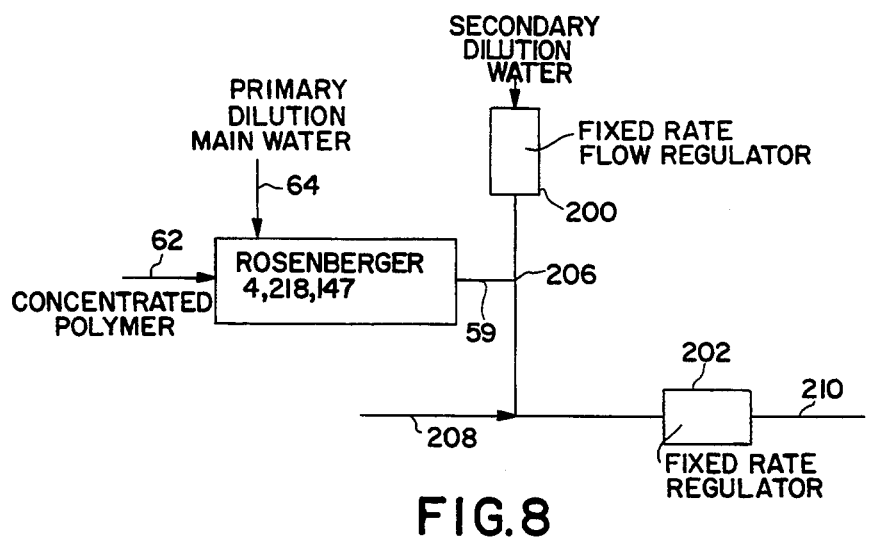
FIG. 8 is a schematic disclosure of a prior at system for introducing secondary delivery.

Heretofore, secondary dilution has been introduced in a manner shown in FIG. 8 which uses the teaching of the polymer inverter of U.S. Pat. No. 4,218,147, which is being used as the basic inversion system. The reference numerals 59, 62, 64 are used to orient FIG. 8 to the system of FIG. 1. It should be understood, however that except for these three reference numerals, the system of FIG. 8 has no relationship to the system of FIG. 1.

In FIG. 8, the introduction of a secondary dilution is controlled by two flow rate regulators 200, 202. The secondary water introduced at 204 is automatically held at a first and fixed flow rate by regulator 200. This water is mixed at a "T" fitting with the inverted polymer solution outflow from pipe 59. Fresh water is also added at 208 to the diluted stream. Finally, a fixed rate regulator 202 releases the secondarily diluted solution at outlet 210.

The trouble with this system (FIG. 8) is that the already inverted polymer goes through the fixed rate regulator 202. At least some of the time, such a regulator is certain to have a relatively high upstream pressure on one side and a relatively low pressure on the other side with a pressure drop between, which causes some degree of shear and therefore changes the characteristics of the inverted polymer. Thus, it is quite likely that the inverted molecules will break as they pass through regulator 202. It is possible to have this kind of control in a primary loop such as loop 24 (FIG. 1). However, once the polymer leaves the closely controlled primary system, the secondary and tertiary effects of randomly occurring variables make it extremely difficult or impossible to effect the same degree of control. Therefore, as a practical matter, the system of FIG. 8 is either totally useless or too sensitive to provide a reliable operation.

Figure 9:
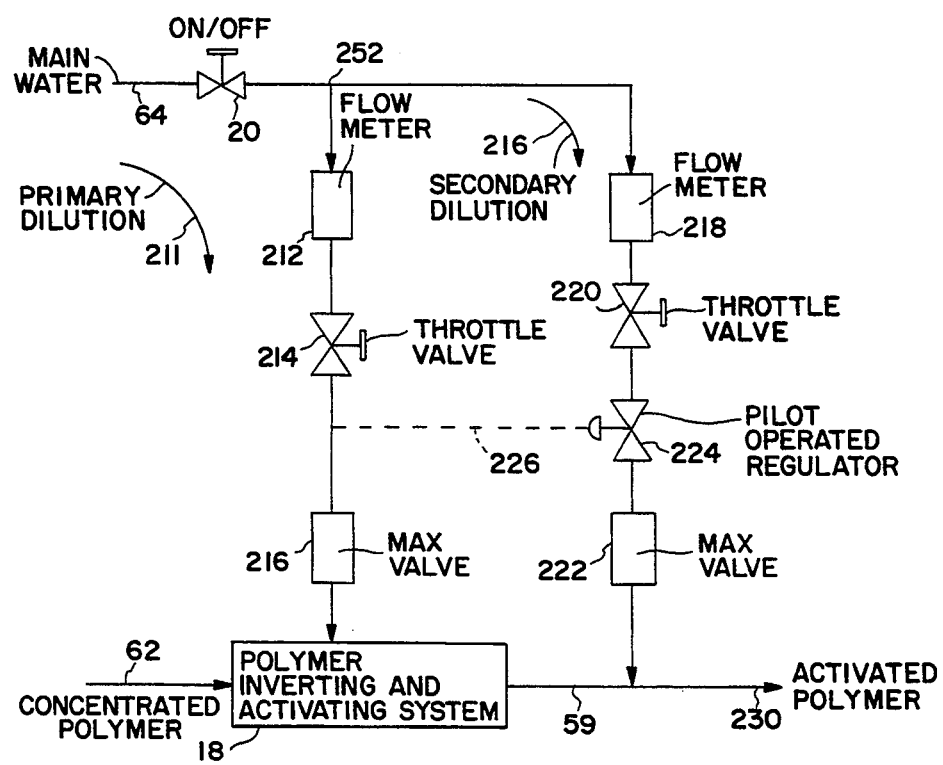
FIG. 9 is a schematic diagram of an inventive system for introducing a diluent via primary and secondary legs.

FIG. 9 shows the inventive secondary dilution system. Again, the reference numerals 18, 59, 62, 64 are used to help orient the relationship between FIGS. 1 and 9. The primary dilution leg 211 (FIG. 9) couples into the (FIG. 1) system at the premix block 26. The secondary dilution leg 216 couples into the output pipe 59 via a simple "T" coupling.

The raw water flow into the FIG. 1 system is via a primary dilution circuit 211 including a flow meter 212, the throttle valve 214, and a maximum flow rate valve 216, which may be a commercial product sometimes identified as a "Dole" valve.

The secondary dilution circuit 216 is as nearly identical as possible to the primary circuit 211, including a flow meter 218, a throttle valve 220, and a maximum flow rate valve 222. In addition, a pilot operated regulator 224 is coupled between the throttle valve 220 and the maximum flow rate valve 222. A pilot line 226 couples the primary dilution circuit 211 to the secondary dilution circuit 216. Thus, it is seen that primary circuit 211 and secondary circuit 216 may be described as a pair of parallel legs having a pilot controlled regulator for delivering the water or other electrolyte fluid to the polymer inverting system in a fixed ratio despite fluctuations.

A conventional regulator 224, such as one made by the Watts Regulator Company of Andover, Mass., has a double chamber sealed by a diaphragm which is exposed on one side to the pressure of a mainstream of water flow. In another chamber is a spring which normally presses against the other side of the diaphragm. If the pressure in the mainstream chamber exceeds the bias of the spring, the diaphragm moves in one direction. If the spring bias exceeds the pressure in the mainstream chamber, the diaphragm moves in the other direction. Depending upon the direction and amount of the diaphragm movement, the mainstream flow rate is increased or decreased to maintain a closely regulated uniformity of the mainstream flow.

Figure 9A:
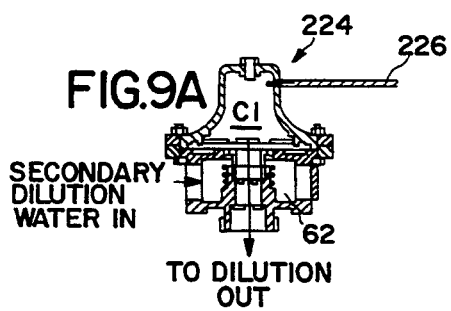
FIG. 9A is a cross-section of a pilot valve used in FIG. 9.

In the pilot flow regulator 224 of the inventive system (FIGS. 9A, 11), the construction is similar except there is no spring. Instead, a pilot line tube 226 is connected to a control chamber C1 in regulator 224 of the primary dilution circuit 211. The mainstream flows through another chamber C2. If the pressure in the primary circuit 211 is higher than the pressure in the secondary circuit 216, the diaphragm D moves in on direction. If it is less, the diaphragm moves in the other direction. The flow of the mainstream is controlled by the movement of the diaphragm. Hence, the pilot regulator 224 keeps the same relationship between the pressures in the primary and secondary circuits 211, 216. This means that the system output at 230 always has the same ratio of primary and secondary dilution water. The various flow meters and maximum valves are set to establish maximum dilution values.

If, for example, the throttle valve 214 is opened or closed a little to simulate changes in water pressure, the pilot operated regulator 224 is observed as immediately opening or closing the secondary dilution circuit 216 in order to restore the preselected ratio of water flowing in the two circuits 211, 216. Thus, an operator may adjust the throttle valve 214 to provide a proper amount of water without unbalancing the system. This greatly simplifies operational procedures. Also, the regulator 224 may respond to and correct for any primary water delivery fluctuation which the system may encounter. First, the upstream source of water 64 may fluctuate. Second, something within the system (FIG. 1) may cause a fluctuation. Third, something downstream, after output 230, may cause an increase or decrease of back pressure upon the system to cause primary water fluctuations.

Figure 9B:
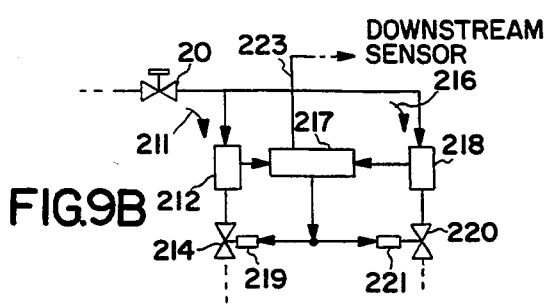
FIG. 9B is part of FIG. 9 with an automatic control for maintaining a ratio of flows in primary and secondary legs of an electrolyte delivery system.

The throttle valves 214, 220 of FIG. 9B have a servo valve controllers 219, 221 (known in the trade as "valve actuators"). These actuators respond to signals transmitted from control circuit 217 to maintain a predetermined relationship between the flow in the primary and secondary legs 211, 216. Therefore, if for example, the ratio of primary to secondary dilution is set at 2:1, and further if a downstream sensor detects an increase in the concentration of the polymer solution, the sensor sends a signal over wire 223 directing circuit 216 to increase the amount of diluting water. The signals sent from circuit 217 to valve actuators 219, 221 increases the flow rates through valves 214, 220 in a ratio of 2:1. The sensor may be placed anywhere in the system which is representative of the final dilution (percentage of solids and water in the final output of the system).

The ratio may also be controlled from a remote location. More particularly, in certain applications the ratio of primary and secondary dilution flows can be critical. For example, in paper making, where polymers are used as retention aids, the final working polymer solution concentration (i.e. after all dilutions are made) must be substantially exact and known in order for the chemical to act favorably on the paper machine. Therefore, a signal processor or operator may control the system.

In this instance, the flow meters 212, 218 on each dilution leg is fitted with a flow transmitter which is in communication with a sensing controller 217, Foxboro (Model 761), Foxboro, Mass. Such flow transmitters are standard commercial items available from Hedland of Racine Wis. The sensing controller may be adjusted from a number of outside sources (e.g. local, remote, etc.) to maintain a selected ratio between the primary and secondary dilution legs. Valve actuators 219, 212 (available from Asahi) fitted to throttling control valves 214 and 220 change the flow rates in response to the sensing controllers commands.

The operator or signal processor sends suitable signals over wire 223 to control, select, and adjust ratios of the flow from an outside source and through the primary and secondary legs.

It is important to note (FIG. 9) that, after inversion, the secondary dilution system does not subject the polymer to any mechanical shear. By an inspection of FIG. 9, it will be seen that an output pipe 59 extends directly from the polymer inverter of FIG. 1 to any suitable activated polymer utilization device without going through any pressure changing devices, such as the regulator 202 of FIG. 8.

Figure 10:
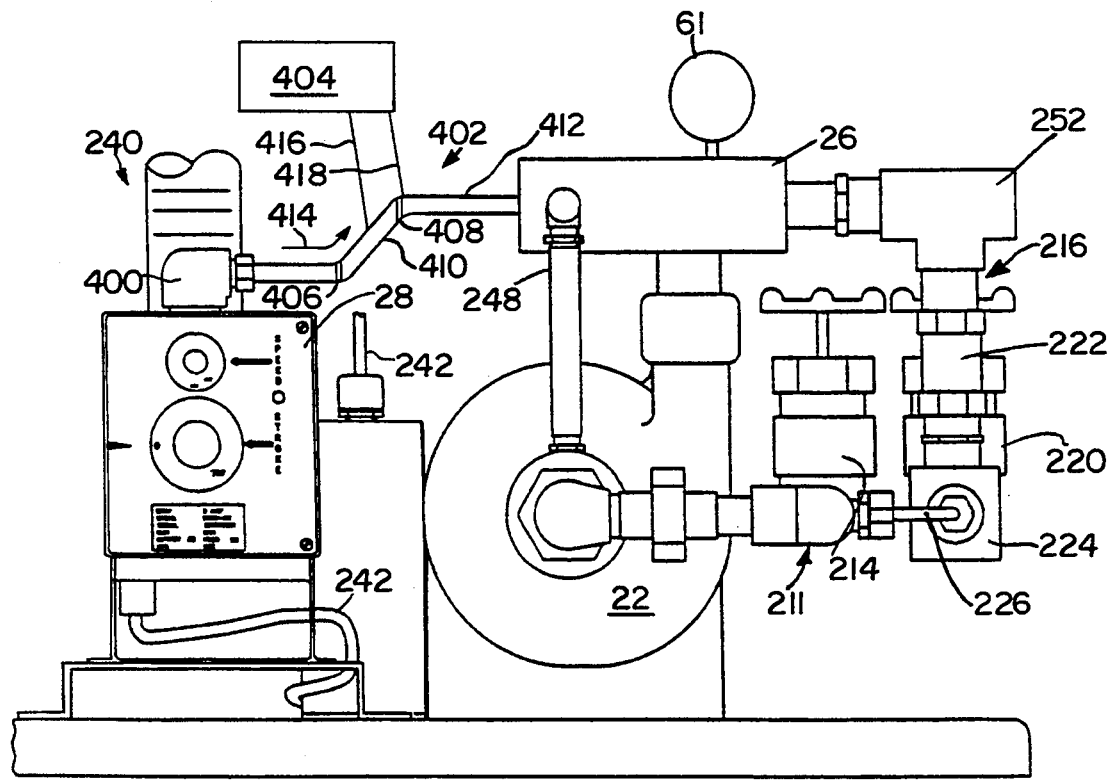
FIG. 10 is a front elevation of the inventive machine having secondary dilution capabilities.
Figure 11:
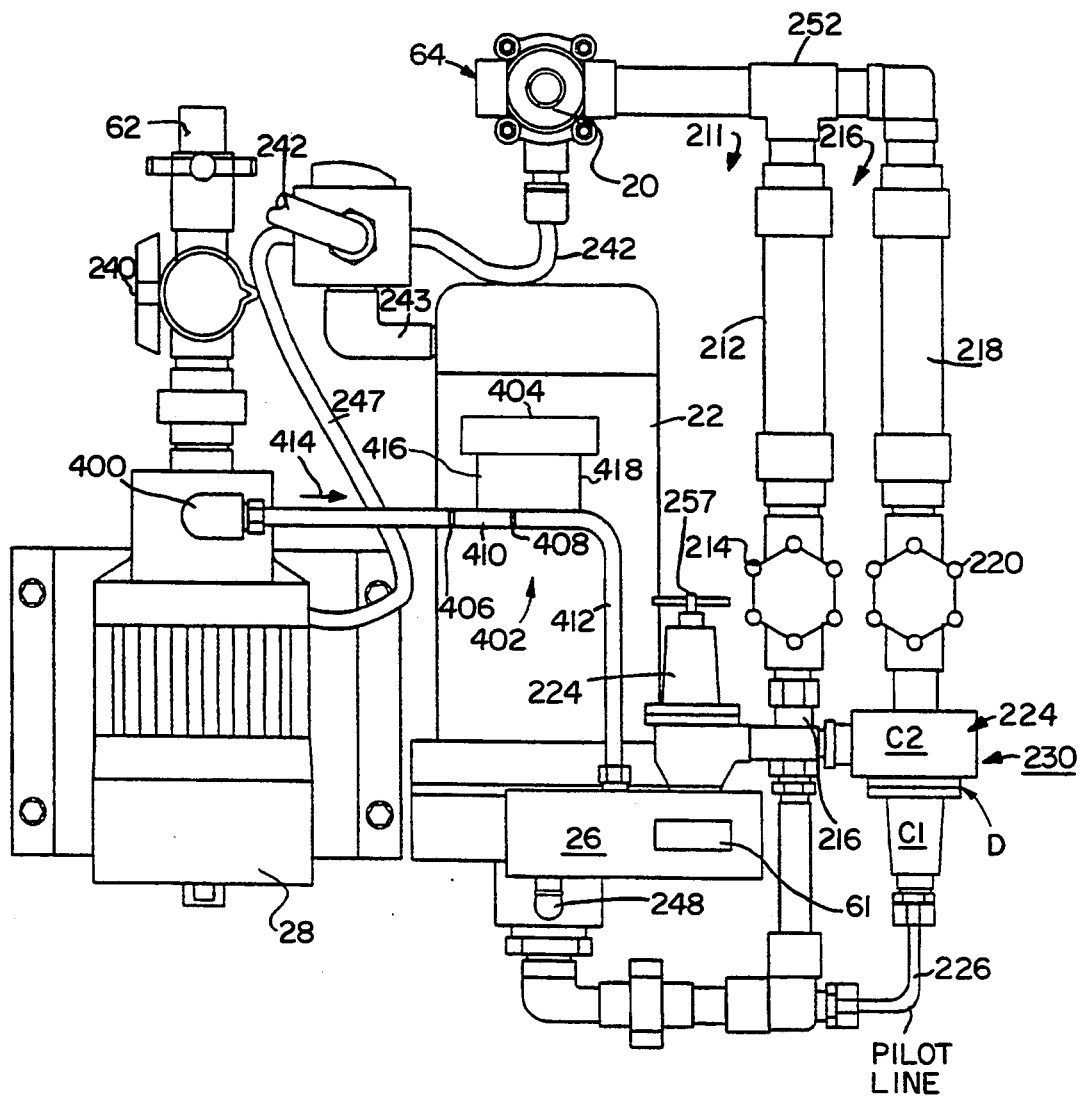
FIG. 11 is a top plan view of the machine of FIG. 10.

The system hardware is seen in FIG. 10 (a side elevation) and FIG. 11, (a top plan view). The raw water intake is at 64 (FIG. 11) and the concentrated polymer intake is at 62. The water is taken in through a solenoid controlled valve 20. The polymer concentrate is taken in through a calibration assembly 240 and a booster pump 28. Electric wires are seen in various o places identified as 242.

The polymer concentrate is pumped into the pre-mix block 26 via a conduit 244 and returned from the block via conduit 248, both of which are part of the loop 24. A pressure gauge is seen at 61. A manual valve 250 provides for adjusting the pressure setting of the pressure regulator 224. A "T" fitting 252 forms the junction between the water intake 64, and the primary and secondary dilution circuits.

The remainder of the hardware may be identified by comparing the reference numbers in FIGS. 8–11.

During the course of the operation of devices that mix, blend and invert liquid polymers, it is necessary to isolate concentrated polymer from the dilution water flowing in the mixing system. This isolation is generally accomplished by using a checking device 400 in a supply line 402 extending between the concentrated polymer supply and the mixing system. This checking device can be a swing check valve, a spring loaded ball or popper, or a simple on/off valve.

When the check valve fails, the water flows back into the polymer supply lines 402, changing the characteristic of the polymer at some measured threshold valve which could result in the improper preparation of the polymer. A suitable relay (not shown) can be engaged for annunciating when a check valve failure is in progress, and also for shutting down the system.

More particularly, check valve 400 prevents a reverse flow of the water through line 402 and back into the concentrated polymer supply source. Under normal circumstances, the check valve may fail from time to time and allow a backflow water seepage to occur. These failures usually result when some form of solid or semi-solid material lodges in the check valve mechanism and stops the valve parts. Such a backflow would lead to a premature wetting of the concentrated polymer which would render the concentrated polymer useless so that it usually has to be discarded. A continued operation of the machine under these conditions usually results in a contamination of the polymer supplies and may cause potential polymer injection pump failures.

According to the invention, means are provided for sensing a change in the characteristic between that of the pure concentrated polymer flowing through line 402 and into the mixing device and that of the polymer that is contaminated with back flowing dilution water. After a polymer is wetted, the water or other electrolyte gives greater conductivity (lower resistivity) to the mixture since a concentrated polymer is usually an effective insulator. Additionally, a physical and chemical change in the polymer occurs when the premature wetting of the polymer causes a certain level of inversion to take place.

In a preferred embodiment of the invention, the resistivity of the polymer is measured by a device which is comprised of two components, a field sensor and a sensor circuit which measures resistivity. An example of such a circuit is manufactured by Curtis Industries, Milwaukee, Wis. and preferably is identified as Model LCS-10, although other circuits in their LOS or LHS lines may be used.

The sensing device is built into a stainless steel tube which is the supply line 402 that interconnects the polymer supply 62 (FIG. 1) and the mixing block 26. A circuit board carrying the sensor circuit 404 is coupled to the stainless steel tube via leads 416, 418 and low voltage electrodes attached to the stainless steel tube.

The principle used by this sensor is to determine the conductivity of the neat polymer stream. For most polymers, the conductivity of a polymer solution changes as water, or another electrolyte, is added to it. Thus, since the highly concentrated, high solids neat polymers are relatively non-conductive, it is possible to measure their electrical current carrying capability to determine when they have become contaminated with water. In one system which was actually built and tested the current resistance was measured by an ohmmeter circuit which measured resistivity in the range of 0-to-100,000 ohms. Other ranges could also be used.

More particularly, the stainless steel tube has two insulation sections 406, 408 which isolate a section 410 of the tube between them. The electrically isolated section 410 doubles as a sensor electrode, the other electrode being the part of the stainless steel tube which is the conduit for the neat polymer being pumped to the premix manifold 26. The polymer is an isolator; therefore, if nothing but polymer appears in the stainless steel tubing extending from pump 28 to block 26, the resistivity between section 410 and tubing 412 is very high.

If the check valve 400 is functioning properly, all polymer flow is in the direction of the arrow 414. There is no back flow of water from the mixing block 26 to the polymer pump 28. If the check valve 400 is not functioning properly, there may be a seepage of water from the block 26 upstream (against the direction of the arrow 414) through tube 402 and toward the pump 28. The water conducts electricity and, therefore, the resistivity goes down, the greater the amount of water, the lower the resistance between section 410 and tubing 412.

The circuit on card 404 applies a voltage on one of the leads 416, 418 and reads the voltage on the other lead. While it does so, it sees the current flow, if any, between its two leads 416, 418. If the check valve 400 is not functioning properly, water in the mixing loop begins to migrate upstream (toward pump 28). Water conducts electricity. Therefore, the electrical signal which is applied to one of the leads 416, 418 transmitted by the wetted polymer across the insulating barrier 408. The circuit on the printed circuit card 404 is basically an ohmmeter designed to measure the resistance across the insulator barrier 408, and thus the amount of water that is backflowing through the check valve. Once the resistance across the barrier falls below a threshold level, a suitable command signal is sent to the system in order to give an alarm, shut down the system, or the like.

In this version, the sensor tube is located between the injection pump head and the check valve. In other versions, it may be located elsewhere. Also, the circuit on board 404 could be an ammeter to measure current or a voltmeter to measure potential difference. Still other techniques could measure upon doppler effect, inductance, capacitance, frequency, or another phenomenon.

Another electrode may be attached to another conductive element in communication with the concentrated polymer conduit. The location of the other electrode may vary with the type of polymer used or the point in the system which is to be monitored, e.g. locating the second electrode close to the injection pump head will monitor contaminated polymer as it approaches the pump head. Therefore, the location of the second electrode, (e.g. close to the check valve, or the injection pump, or even the bulk tank supply vessel) is fundamental in determining the point of alarm in the system.

Figure 10A:
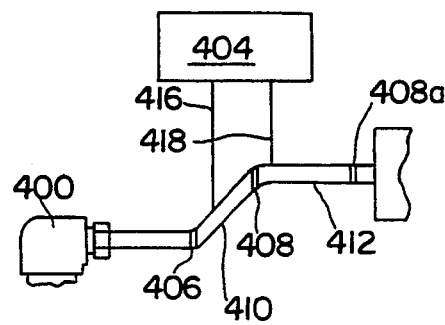
FIG. 10A shows an alternative wet polymer sensor for use in FIG. 10.

The principles of the sensor 402 which are shown in FIG. 10 may be expanded to give more detailed information. For example, in FIG. 10A a third isolator 408a is added to the stainless steel pipe, thereby making two isolated conductive sections 410, 412 which are connected to leads 416, 418, respectively. The process may be expanded so that any suitable member of isolated sections may be provided. This way, the system may monitor the progress of water seeping back toward the source of the polymer. Thus, the system may be adapted to give different command signals depending upon how serious the problem becomes.

Ideally, all parts of the conductive conduit should normally be made of similar metals, but this is not necessary. In one embodiment the sensor board has a potentiometer that may adjust the sensitivity of the circuit to enable an operator to compensate for increased or decreased polymer conductivity, dilution water conductivity, or the concentrated polymer conduit's electrical resistivity.

Those who are skilled in the art will readily perceive how to modify the invention. Therefore, the appended claims are to be construed to cover all equivalent structures which fall within the true scope and spirit of the invention.

I claim:

1. The claimed invention is a method of inverting and activating polymer compositions containing polymer gel particles dispersed in an emulsion or solution form, said method comprising the steps of (a) receiving polymer and a diluent,
    (b) providing a conduit path including a closed pressurized feedback loop within said path,
    (c) combining said polymer with said diluent to cause a homogenous blending thereof within said conduit path,
    (d) said homogenous blending of step (c) including the steps of:
        (d1) premixing to blend said polymer and said diluent in said conduit path which contains both said polymer and a mixture comprised of polymer/diluent;
        (d2) continuously blending said Polymer/diluent mixture in said feedback loop of said conduit path at a level of pressure and mixing energy which inverts and activates said polymer, said pressure and energy being developed by a derated centrifugal pump coupled to receive the polymer/diluent mixture flowing in the conduit path and for mixing a continuous input of said diluent with said polymer/diluent mixture; and
        (d3) recycling a portion of said polymer/diluent mixture in said pressurized feedback loop of said conduit path;
    (e) maintaining and controlling 5-70% by volume of a returned output from the derated centrifugal pump and returning said returned output through said feedback loop of said conduit path to said premixing step (d1); and
    (f) final stage processing of said homogeneously blended polymer and diluent by passing a non-returned 95-30% by volume of the derated centrifugal pump output through a pressure regulator which rapidly reduces the output pressure of said homogeneously blended polymer and diluent in order to invert and activate the polymer compositions.

2. The method of claim 1 wherein step (d2) further comprises pumping said mixture in said derated pump at a derated factor wherein the pumping capacity of a corresponding centrifugal pump is reduced in the order of approximately 2-7 times (50% to 14%) of a normal pumping volume and with full normal pumping energy.

3. The method of claim I and the further steps following step of conveying twin streams of diluent via two parallel paths forming primary and secondary legs of diluent flow, and controlling one of said twin streams of diluent responsive to a pilot flow of diluent from the other of said twin streams, said pilot flow indicating pressure in said other of said twin streams, said controlled one of said twin streams of diluent holding a predetermined ratio of polymer to diluent in an outflowing stream of said polymer compositions.

4. The method of claim 3 and the further steps of infinitely varying said diluent flow in said secondary leg within a predetermined range of flow rates.

5. The method of claim 3 and the further steps of infinitely varying said flow in said primary leg within a predetermined range of flow rates.

6. The method of either claim 4 or 5 and the further steps of automatically maintaining a selected ratio of said primary and secondary flow rates in response to remote signals responsive to volumes of diluent in said twin streams.

7. The method of claim 3 and the further step of regulating a throttle valve and a maximum flow control valve in one of said legs in response to said pilot flow from the other of said legs for controlling the flow in said one of said legs.

8. The method of claim 3 and the further steps one adjusting the flow rates through said primary and secondary legs to a selected ratio in response to sensing a selected concentration of said polymer compositions in an output flow, and automatically maintaining said selected ratio in response to said sensed concentration.

9. A four step method of inverting and activating polymer compositions containing polymer gel particles, said method comprising the steps of:

(a) premixing water and a polymer in a mixing manifold containing a static mixer and circulating the resulting mixture in a pressurized feedback loop including said mixing manifold and a derated centrifugal pump, said pump having a substantial blade activity for imparting a level of pressure and mixing energy which inverts and activates said polymer relative to a volume of outflow from said pump;
    (b) blending the output of said manifold in said pump;
    (c) recycling a substantial portion of the outflow of said pump through said pressurized feed back loop and mixing manifold, and
    (d) directing the remaining portion of the outflow of said pump through a pressure regulator which continuously adjusts the outflow for maintaining a constant upstream pressure while providing a sudden and downstream relaxation of the pressure imparted by said pump whereby said polymer is inverted and activated by said sudden relaxation of pressure.

* * * * *